(12) United States Patent
Khaiat et al.

(10) Patent No.: US 7,252,831 B2
(45) Date of Patent: Aug. 7, 2007

(54) TOPICAL TREATMENT OF INGROWN HAIRS

(75) Inventors: Alain V. Khaiat, Singapore (SG); Anna Gomes, Earlwood (AU); Vaishali Bhide, Maharashtra (IN); Catherine Salerno, Millington, NJ (US); Victoria Dole, Whitehouse Station, NJ (US)

(73) Assignee: J&J Consumer Companies, Inc., Skillman, NJ (US)

( * ) Notice: Subject to any disclaimer, the term of this patent is extended or adjusted under 35 U.S.C. 154(b) by 0 days.

(21) Appl. No.: 11/451,163

(22) Filed: Jun. 12, 2006

(65) Prior Publication Data

US 2006/0228321 A1    Oct. 12, 2006

Related U.S. Application Data

(63) Continuation of application No. 10/844,809, filed on May 13, 2004, now abandoned, which is a continuation-in-part of application No. 10/663,238, filed on Sep. 16, 2003, now abandoned, which is a continuation-in-part of application No. 10/439,735, filed on May 16, 2003.

(51) Int. Cl.
*A61K 8/02* (2006.01)
*A61K 8/19* (2006.01)
*A61K 8/97* (2006.01)
*A61Q 9/00* (2006.01)
*A61Q 5/00* (2006.01)

(52) U.S. Cl. .................... 424/401; 424/70.1; 424/70.8; 424/73; 424/74; 514/864; 514/880

(58) Field of Classification Search .................... None
See application file for complete search history.

(56) References Cited

U.S. PATENT DOCUMENTS

| | | | | |
|---|---|---|---|---|
| 4,944,939 | A | * | 7/1990 | Moore .......................... 424/73 |
| 5,200,429 | A | * | 4/1993 | Sato et al. ................... 514/766 |
| 5,543,417 | A | | 8/1996 | Waldstreicher |
| 6,227,362 | B1 | | 5/2001 | Cheung |
| 6,271,246 | B1 | | 8/2001 | Murad |
| 6,846,812 | B2 | * | 1/2005 | Dalko et al. ................ 514/171 |
| 2001/0031283 | A1 | | 10/2001 | Belcheff |
| 2003/0018339 | A1 | | 1/2003 | Higueras et al. |
| 2003/0180339 | A1 | | 9/2003 | Khalat et al. |
| 2004/0167498 | A1 | * | 8/2004 | Azar et al. ..................... 606/9 |
| 2004/0191208 | A1 | | 9/2004 | Courtin |
| 2004/0234632 | A1 | | 11/2004 | Piccirilli et al. |

FOREIGN PATENT DOCUMENTS

| | | |
|---|---|---|
| CN | 1342392 A | 4/2002 |
| EP | 0 281 812 A1 | 9/1988 |
| EP | 1 210 937 A2 | 6/2002 |
| EP | 1 269 991 A2 | 1/2003 |
| FR | 2 826 579 A1 | 1/2003 |
| WO | WO 01/82882 A1 | 11/2001 |
| WO | WO 02/05773 A1 | 1/2002 |
| WO | WO 03/026605 A2 | 4/2003 |
| WO | WO 03/041669 A1 | 5/2003 |
| WO | WO 03/084553 A1 | 10/2003 |

OTHER PUBLICATIONS

Chan et al. The analgesic and anti-inflammatory effects of Portulaca oleracea L. subsp. Sativa (Haw.) Celak. J Ethnopharmacol. Dec. 2000; 73(3): 445-51.*
K. Chan et al., The analgesic and anti0inflammatory effects of Portulaca oleracea, Journal of Ethnopharmacology 73 (2000), pp. 445-451.
Alison M. Layton, Optimal Management of Acne to Prevent Scarring and Psychological Sequelae, Am J. Dermatol 2001; 2, pp. 135-141.
U.S. Appl. No. 10/844,809 filed May 13, 2004, Johnson & Johnson Consumer Companies, Inc.
U.S. Appl. No. 10/663,238 filed Sep. 16, 2003, Johnson & Johnson Consumer Companies, Inc.
U.S. Appl. No. 10/439,735 filed May 16, 2003, Johnson & Johnson Consumer Companies, Inc.
International Search Report dated Nov. 16, 2004, for corresponding PCT application PCT/US2004/015053.
International Search Report dated Nov. 16, 2004, for corresponding PCT application PCT/US2004/015054.

* cited by examiner

*Primary Examiner*—Michael G. Hartley
*Assistant Examiner*—Jake M. Vu

(57) ABSTRACT

This invention relates to improved compositions and methods for preventing or inhibiting the development of ingrown hairs or razor bumps in skin subjected to hair removal techniques by applying compositions containing sebum reduction agents; keratolytic agents and anti-inflammatory agents.

5 Claims, 6 Drawing Sheets

TOPICAL TREATMENT OF INGROWN HAIRS

CROSS REFERENCE TO RELATED APPLICATIONS

This application is a continuation of prior application Ser. No.: 10/844,809, filed May 13, 2004, now abandoned which is a continuation-in-part of prior application Ser. No. 10/663,238 filed Sep. 16, 2003, now abandoned which is a continuation-in-part of prior application Ser. No. 10/439,735 filed May 16, 2003, which are hereby incorporated by reference in their entirety.

FIELD OF THE INVENTION

This invention relates to the treatment of skin and, more particularly, to the treatment of conditions of skin caused by excess sebum production and the consequences thereof, including the condition of acne vulgaris.

Excess sebum production is a common problem particularly with teenagers, leading to an oily/shiny appearance of the skin. This causes embarrassment and is also one of the principal factors contributing to acne. It is believed that acne is a result of a number of factors. We now understand that sebum production occurs in the sebaceous glands through the presence of the 5-alpha-reductase enzyme. This enzyme is sensitive to the level of testosterone penetrating sebaceous cells. The testosterone is transformed to dihydrotestosterone under the influence of the 5-alpha-reductase enzyme, leading to an abundance of sebum. Sebum consists of a mixture of squalane wax esters, cholesterol esters, and triglycerides. An abnormally high rate of sebum supports the growth and proliferation of *Propionibacterium acnes*, which degrades sebum triglycerides to diglycerides, monoglycerides and free fatty acids. The free fatty acids peroxidize in the presence of free radicals, leading to an oily appearance, inflammation, comedones and other acne manifestations. By inhibiting the lipase activity, oiliness of the skin and the consequences thereof of the skin may in turn be inhibited even where sebum production is not simultaneously controlled.

More recently, topical agents have been studied and found to have activity as oil controlling agents. One of these is elubiol (dichlorophenyl-imidazoltioxolan). Elubiol is an effective oil control agent. Regulatory approval is being sought for its use for this purpose.

Some alternative sebum-regulating agents have been described in U.S. patent application Ser. No. 10/340,341 (filed Jul. 13, 2001), the subject matter of which is incorporated herein by reference. That invention provides a number of different products which have sebum regulating effects, including a hydrolyzed vegetable protein produced by enzymatic hydrolysis. Such hydrolyzed vegetable proteins include soy protein and wheat protein. Such compositions could also include other active agents designed to assist in improving skin appearance and assist in inhibiting the development of other conditions, such as acne, such as keratolytic agents, including salicylic acid, benzoyl peroxide, resorcinol, colloidal sulphide, selenium disulphide, sulfur and anti-inflammatory agents such as alpha-bisabolol, dipotassium glycyrrhizinate, allantoin, matricaria (*chamomilla recutita*) extract, tocopheryl acetate, green tea (*camellia sinesis*) extract, and turmeric (*curcuma longa*) extract.

We have discovered that combinations of certain of the compositions set forth in U.S. patent application Ser. No. 10/340,341 with additional active agents unexpectedly demonstrate significantly faster and more complete relief from acne conditions with low occurrence of inflammation than previously known.

Thus, this invention relates to providing compositions for application to the skin to inhibit or regulate sebum production, to inhibit or treat oily skin, to prevent or inhibit the development of acne and to treat acne when present. This invention further relates to a method of preventing, controlling or inhibiting the oily/shiny appearance of skin and consequential disorders resulting therefrom, such as acne.

Unless the context clearly requires otherwise, throughout the description and the claims, the words "comprise", "comprising" and the like are to be construed in an inclusive sense as opposed to an exclusive or exhaustive sense; that is to say, in the sense of "including, but not limited to".

SUMMARY OF THE INVENTION

Surprisingly, it has been found that the topical application of compositions containing a sebum regulator, a keratolytic agent and an anti-inflammatory agent results in unexpectedly superior control of skin conditions such as acne. More particularly, the compositions and methods of this invention relate to formulations containing a sebum regulator, a keratolytic agent, an anti-inflammatory agent and a bacterial lipase inhibitor and, more preferably a sebum regulator, a keratolytic agent, an anti-inflammatory agent, a bacterial lipase inhibitor and a bacterial proliferation inhibitor which can be applied topically to skin which has been affected by certain skin conditions such as acne. Surprisingly, the compositions and methods of this invention provide extremely rapid results in resolving lesions associated with acne vulgaris.

More preferably, the compositions of this invention relate to products containing a sebum regulator which is a 5-alpha-reductase inhibitor. Such 5-alpha-reductase inhibitors may include amino acids, more particularly, glycine derivatives in combination with cinnamon bark extract. Further, the compositions of this invention preferably contain a keratolytic including salicylic acid. Such compositions also contain an anti-inflammatory agent such as portulaca extract.

More preferably, the compositions of this invention also contain a lipase inhibitor such as cedarwood extract or hydrolyzed vegetable proteins. The compositions of this invention may also preferably include a bacterial proliferation inhibitor in addition to salicylic acid, which may have such activity.

The compositions of this invention can be useful in controlling or at least inhibiting the oily nature of skin, and inhibiting, or controlling, consequences thereof such as acne, containing the foregoing ingredients. This invention also includes a method of treating acne or at least inhibiting it and a method of preventing the development of oily skin by applying the compositions of this invention to skin susceptible to developing excess oiliness.

The compositions of this invention may also be useful in controlling or at least inhibiting the development of ingrown hairs due to shaving with razors, waxing or hair removal using a depilatory product, including a chemical depilatory product (i.e., *Pseudofolliculitis barbae*) on various parts of the body, including face, underarms and in the "bikini" or groin region.

DETAILED DESCRIPTION OF THE PREFERRED EMBODIMENTS

Figure 1:
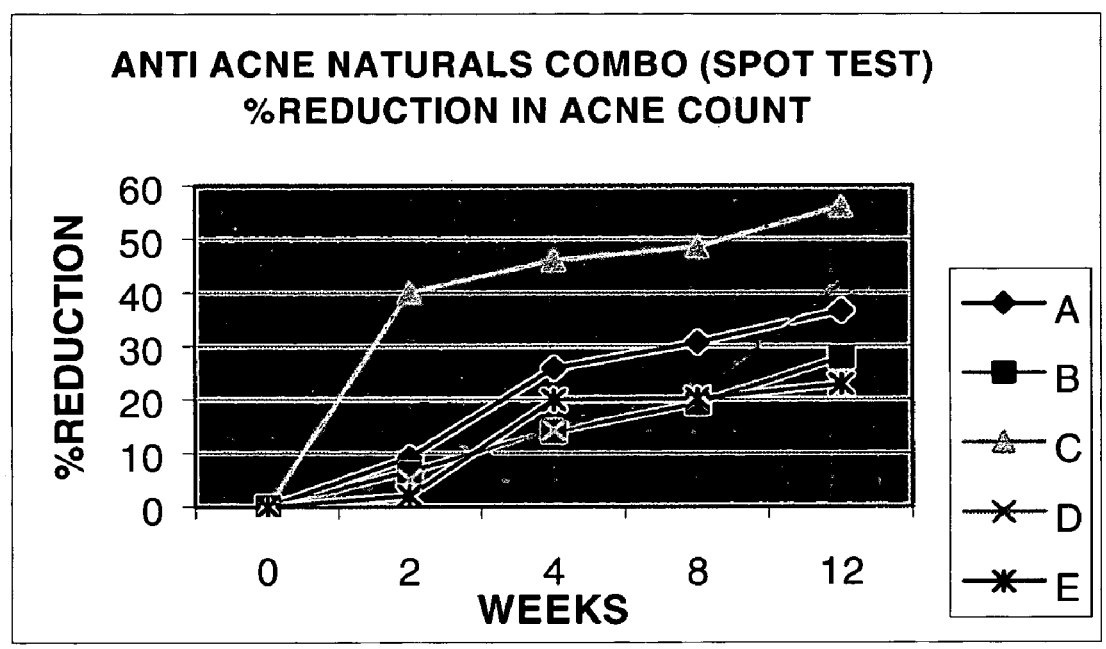
FIG. 1 is a graph illustrating the percent reduction in acne count pursuant to testing set forth in Example 2.

The compositions of this invention can contain other ingredients normally present in formulations for skin application as will be elaborated below in discussing compositions for use in all aspects of the invention.

More particularly, it has been found that a combination of sebum control agents, anti-inflammatories and keratolytic agents unexpectedly serve to reduce the time for acne lesions to heal and to reduce the amount of acne lesions more quickly than previously-known compositions. The compositions of this invention may also preferably contain bacterial lipase inhibitors and, in addition, bacterial proliferation inhibitors.

Sebum control agents are utilized in the compositions of this invention that regulate the sebum production rate via the pathway of 5-alpha-reductase inhibition.

More preferably, such 5-alpha-reductase inhibiting sebum regulating agents may also be obtained synthetically, such as from amino acid derivatives. In particular, glycine derivatives have been found to be useful in the compositions of this invention. More particularly, a combination of capryloylglycine and methylglycine has been found to be useful in reducing sebum production. Other products that inhibit the 5-alpha-reductase enzyme may also useful in the compositions and methods of this invention.

Sebum regulating agents may, more preferably, contain both naturally-derived and synthetically-derived materials. Most preferable is the combination of glycine derivatives and cinnamon zeylanicum bark extract. This composition is commercially available as Sepicontrol A5 from Seppic of Paris, France.

It is thought that the presence of glycine, an essential amino acid, reinforces the cutaneous barrier. The lipoamino structure is well tolerated by the skin, thereby helping to restore the skin to its normal balance. The catechinic tannin content in the cinnamon extract acts as an astringent and stimulant for cutaneous cells. We believe that the combination of amino acid and cinnamon extract acts as a bacterial proliferation inhibitor as well.

Bacterial lipase inhibitors are also useful in the compositions of this invention. Lipase inhibition is believed to be a mechanism by which the hydrolyzed vegetable proteins such as hydrolyzed soy protein and hydrolyzed wheat protein and the plant extracts such as those from cedar and poplar achieve oil control, at least in part. Application of an agent to inhibit lipase activity is believed to be a novel approach to controlling oily skin. Sebum regulating agents can be derived from a natural source such as from a plant, in particular, hydrolyzed vegetable protein such as hydrolyzed cereal protein, in particular, hydrolyzed wheat protein or from other plants such as hydrolyzed soy protein produced by any means such as acid, bacterial or enzymatic hydrolysis. Certain plant extracts are also included within the scope of the invention, such as extracts from suitable trees, including cedar, poplar and mimosa. Such extracts can be from the foliage or from the various stages of the flower of the particular tree, in particular from the bud. Extracts useful in the compositions and methods of this invention may also be obtained from the bark of trees.

Amino acid/tannin-containing materials are useful as bacterial lipase inhibitors, in addition to the hydrolyzed vegetable proteins set forth above.

Hydrolyzed cereal proteins useful as bacterial lipase inhibitors and/or excess sebum regulators in the compositions and methods of this invention can be a hydrolyzed wheat proteins, produced by any hydrolysis method such as soluble wheat proteins, preferably of a high molecular weight type having a molecular weight in the region of 100,000 to 500,000 Daltons, but lower molecular weight hydrolysates are also believed to be effective. High molecular weight products sold by Croda such as Tritisol having a molecular weight of 100,000 Daltons and Tritisol XM having a molecular weight of 500,000 are particularly suitable. We believe that the bacterial lipase inhibitor increases the level of triglycerides, which provides a feedback signal to the sebaceous glands.

The compositions of this invention also preferably contain bacterial proliferation inhibitors. These materials restore the cutaneous ecosystem to a more normal balance and thus inhibit bacterial proliferation. Mild bacteriostatic compounds such as salicylic acid, and the like are useful in the compositions and methods of this invention. Also useful are glycine derivatives and cinnamon bark extract, as they effect a bacteriostatic activity. Other bacterial proliferation inhibitors include the following: tea tree oil as well as antibiotics known to those of skill in the art, including, for example, erythromycin and clindamycin and the like.

Anti-inflammatory agents are also a preferred ingredient of the compositions and useful in the methods of this invention. Any suitable topical anti-inflammatory agent may be used in accordance with this invention. Preferred for their effectiveness, availability and regulatory approval status are glycine derivatives and cinnamon bark extract, alpha-bisabolol and portulaca extract and combinations thereof. Preferably, portulaca is present in the compositions of this invention. More preferably, both alpha-bisabolol and portulaca are present. Also useful may be allantoin. These agents will be present in effective amounts and the amount will depend upon the effectiveness of the particular substance.

Keratolytic agents are also preferably used in the compositions of this invention. The keratolytic agent can be any suitable agent, including but not limited to, benzoyl peroxide, resorcinol, colloidal sulphur, selenium disulphide, sulfur and, more preferably, because of its effectiveness and mildness, salicylic acid.

Preferably, the compositions of this invention contain a sebum-reduction agent, a bacterial lipase inhibitor, a bacterial proliferation inhibitor, an anti-inflammatory agent and a keratolytic agent. More preferably, the compositions of this invention contain a synthetically-derived sebum regulating agent, a hydrolyzed vegetable protein, a naturally-derived bacterial lipase inhibitor, a keratolytic agent, and an anti-inflammatory compound.

Even more preferably, the compositions of this invention contain a sebum regulating agent which is an amino acid derivative combined with a naturally-derived sebum regulating agent, at least one bacterial lipase inhibitors chosen from the group of cedarwood extract, hydrolyzed vegetable protein or a mixture of two or more; salicylic acid as a bacterial proliferation inhibitor; portulaca as an anti-inflammatory agent and salicylic acid as a keratolytic agent.

In another aspect of this invention, there is provided the use of the compositions of this invention and a deposition enhancer for preventing, inhibiting or controlling the oily/shiny appearance of skin and/or the consequences thereof such as acne. In this aspect, there is also provided a topical composition for such use comprising at least one sebum regulating agent and a deposition enhancer together with a suitable carrier. Also provided is a method for preventing or at least inhibiting oily skin and/or the consequences thereof such as acne, comprising the topical application of a sebum regulating agent and a deposition enhancer such as phytantriol, polyquaternium-6, -7, -22 and -39. Preferably, the deposition enhancer is phytantriol.

In accordance with another aspect of this invention, there is provided a method of controlling the oily/shiny appearance of skin comprising applying to the skin having such appearance or susceptible to such disorder, the compositions of this invention containing a lipase inhibiting substance. This aspect of the invention also provides a topical composition for use in such a method comprising a lipase inhibitor and a suitable carrier. Lipase inhibition is believed to be a mechanism by which the hydrolyzed vegetable proteins such as hydrolyzed soy protein and hydrolyzed wheat protein, the plant extracts such as those from cedar and poplar and synthetically-derived amino acid-containing compositions achieve oil control, at least in part. Application of an agent to inhibit lipase activity in connection with the other active agents of the compositions of this invention is believed to be a novel approach to controlling oily skin.

Without wishing to be bound by any theory, it is believed that the activity of the oil control agents of this invention in all its aspect, modulate the rate of sebum production through the follicular reservoir and through inhibiting lipase activity, or possibly also at the sebum synthesis step.

In accordance with the compositions and methods of this invention, the active ingredients for controlling the oiliness of the skin are preferably applied in an amount of between about 2 and about 4 $\mu l/cm^2$, preferably about 3 $\mu l/cm^2$. The active ingredients can be applied at intervals to achieve effective results. Desirably, application will be at least once a day, or preferably twice a day. Treatment periods will depend on the severity of the condition and also whether the active ingredient is being applied as a preventative measure for the development of oily skin or after oily skin has emerged or the more serious acne manifestation exists. Because the active ingredients of the invention are found to be mild and non-aggressive agents for treating these disorders of the skin, application will need to be for a significant period of time. This time may vary from person to person. Trials have shown that significant reduction in oily appearance of the skin can occur after only four weeks.

The active ingredients of the invention in all its aspects will be applied in topically applicable compositions. The compositions can be applied on skin directly without any other preparation. It is believed that the active ingredients will work more quickly if the skin is thoroughly cleaned for application of the active ingredients, for a period of from one day up to about two weeks prior to commencement of application of the active agent. A suitable wash out conditioning material is that supplied by Johnson & Johnson under the trademark Clean & Clear® Facial Wash. During application of the active ingredient, the face is washed and then thoroughly dried before application of the active agent in the topical formulation. The topical formulation, dependent on its nature, can be simply applied with a finger or through incorporation in a suitable substrate such as a suitable fabric.

The topical formulations of the invention can be in any desired form such as a gel, cream, lotion, liquid or atomizer spray. These compositions can contain other agents which have an oil control or other useful effect in the complex system of excess oiliness and the consequences thereof such as acne. These agents should not interfere with the effectiveness of the active agents of the current invention.

The compositions of this invention may be applied in the form of alcohol-based gels as well as aqueous gels. For example, in a preferred embodiment of this invention, a sebum control agent, a keratolytic agent, and an anti-inflammatory agent may be combined with alcohol-based solvents including lower alcohols (e.g., ethyl alcohol, isopropyl alcohol, hamamelis virginiana and the like). Preferably, there should be from about 30 to about 50% by weight of alcohols in the compositions of this invention and from about 30 to about 45% by weight of hamamelis virginiana. More preferably, the compositions of this invention further contain a bacterial lipase inhibitor. Sebum control agents, keratolytic agents, anti-inflammatory agents and bacterial lipase inhibitors may be preferably chosen from 5-alpha reductase inhibitors, salicylic acid, portulaca extract or alpha bisabolol and cedarwood extract or hydrolyzed vegetable protein, respectively. Most preferably, said sebum control is capryloyl glycine, *Cinnamomum zeylanicum* bark extract and Sarcosine; said keratolytic agent is salicylic acid, said anti-inflammatory is portulaca extract and said bacterial lipase inhibitor is cedarwood extract. Said alcohol-based gels may contain hydroxyalkyl cellulose thickening agents, including hydroxypropylcellulose and hydroxyethylcellulose; alkylene glycols, including butylene glycol and propylene glycol as additional solvents; and humectants such as glycerin. Buffering agents known to those of skill in the art may also be utilized to adjust pH, such as sodium hydroxide and sodium citrate.

The active agents of the compositions and methods of the invention are present in the topical compositions in an amount effective to achieve the desired result. The higher the concentration, the more rapid the desired effect will be achieved. However, above certain levels; dependent upon the particular product, increased activity becomes marginal, may possibly increase the probability of side effects, and additional active agent may be wasteful. Generally observable effects can be achieved at from about 0.1% to about 1% of active ingredients. More preferably, less than about 5% active ingredient level should be present and most preferably, less than about 3% active ingredient should be present. However, the ranges of active ingredients generally vary depending upon the particular ingredient used. In general, there should be sufficient active ingredient present in the compositions of this invention to be effective for the purpose of utilizing the compositions. There should be less active ingredient present than would cause side effects such as irritation, inflammation or other negative activities. Preferably, sebum regulating agents are present in the compositions and methods of this invention in amounts effective to provide anti-inflammatory activity. Of course, these agents will be present in effective amounts, which depend upon the effectiveness of the particular substance. If Sepicontrol A5 is used in the methods and compositions of this invention, it should be present in an amount of from about 0.5% to about 5% by weight of the composition, and more preferably, from about 1% to about 4% by weight of the composition.

Materials useful as bacterial lipase inhibitors are preferably present in the compositions and methods of this invention in amounts effective to provide anti-inflammatory activity. Of course, these agents will be present in effective amounts, which depend upon the effectiveness of the particular substance. If cedarwood extract is used with hydrolyzed vegetable proteins such as wheat protein and soy protein, the total amount of these three materials should be present in an amount of from about 0.1% to about 4% by weight of the composition, preferably from about 0.5% to about 3% by weight of the composition.

Many of the materials which affect bacterial lipase activity and keratolytic activity also work to inhibit bacterial proliferation, including Sepicontrol A5 and salicylic acid, tea tree oil, as well as antibiotics such as erythromycin and clindamycin and the like. These materials include . . . and should be present in the compositions and methods of this invention in amounts effective to provide bacterial proliferation inhibition activity. If salicylic acid is used, for example, it should be present in an amount of from about 0.5% to about 2% by weight of the composition.

Preferably, anti-inflammatory agents are present in the compositions and methods of this invention in amounts effective to provide anti-inflammatory activity. Of course, these agents will be present in effective amounts, which depend upon the effectiveness of the particular substance. If *Portulaca oleracea* extract is used, it should be present in an amount of from about 0.2% to about 3% by weight of the composition, more preferably from about 0.5% to about 1% by weight of the composition. If alpha bisabolol is used, it should be present in an amount of from about 0.1% to about 3% by weight of the composition, more preferably, from about 0.1% to about 1% of the composition.

Keratolytic agents should be present in the compositions and methods of the invention in effective amounts. Preferably, they should be present in an amount of from about 0.1% to about 2% by weight of the composition. More preferably, they should be present in an amount of at least about 0.2%, more preferably at least about 0.3% and most preferably at least about 0.5%. The maximum amount will be limited generally by cost factors as excess will be unnecessary to achieve the required result and may lead to unwanted side-effects. Most preferably, the keratolytic agent is salicylic acid.

Most preferably, the compositions of this invention contain Sepicontrol A5; a bacterial lipase inhibitor selected from the group consisting of cedarwood, hydrolyzed soy protein and hydrolyzed wheat protein; salicylic acid; and portulaca extract. Such compositions have been shown to have unexpected results in achieving reduction in the amount of acne in a very short period of time.

Other components that may be useful in the compositions and methods of this invention include a deposition enhancer such as phytantriol and polyquaternium-6, -7, -22 and -39. Preferably, phytantriol is present in the compositions and methods of this invention in an amount of from about 0.1 and about 0.5%, more preferably from about 0.1 and about 0.3% by weight of the composition.

Another desirable component of the compositions is a skin penetrant substance such as propylene glycol or transcutol the penetrant assists in ensuring the compositions of the invention penetrate to the pores of the skin to achieve the desired result.

The compositions of this invention will preferably contain other components, normally present in skin treatment composition such as thickeners, emulsion stabilizers, emulsifiers, emollients, occlusive agents, skin conditioners, moisturizers, humectants, preservatives, antioxidants, pH adjusting agents, surfactants, chelating agents, tackifying agents and fragrances and the like. Desirably the compositions are aqueous based. Since some of the ingredients are not water miscible, the compositions will need to be formed into an emulsion using suitable emulsifying apparatus as is well known in the art, or as water miscible organic solvent added to dissolve the water immiscible ingredients.

The compositions of this invention may be used in conjunction with other active ingredients and in conjunction with other treatment regimens, including without limitation, tretinoin application. Such active ingredients may also be incorporated into the compositions of this invention. The compositions of this invention may be applied to the skin using the hand directly or may be applied to the skin in conjunction with an applicator device such as a wipe or swab or the like. The compositions of this invention may be packaged in a tube, a sealed packet, a jar, a pump, a bottle, a can, a pledget, a towelet, a wipe or the like. The compositions of this invention may be utilized in different forms, including as a skin cleanser, as a skin toner, as a moisturizer or leave-on treatment or the like.

Thickeners include suitable polymers such as Carbomer, hydroxypropyl methylcellulose, hydroxyethylcellulose, PVM/MA decadiene cross-polymer and Acrylates/$C_{10\text{-}30}$ Alkyl Acrylate cross-polymer in an amount generally between about 0.15 to about 1.5%, more preferably about 0.45 to about 1.3%, most preferably about 0.15 to about 1%. Two or more of such thickeners can be added. In some cases the thickeners have other effects such as being emulsion stabilizers. Other specific emulsion stabilizers may also be added. A preferred combination is the PVM/MA decadiene cross-polymer and the Acrylates/$C_{10\text{-}30}$ Alkyl Acrylate cross-polymer. PVM/MA decadiene is usually present in an amount between about 0.15 to about 0.5%, more preferably between about 0.15 to about 0.3%. Acrylates/$C_{10\text{-}30}$ Alkyl Acrylate cross-polymer is usually present between about 0.3 to about 0.8%, more preferably between about 0.5 to about 0.7%.

Another desirable ingredient is an emollient, such diisopropyl adipate/isohexadecane dimethicone and $C_{12\text{-}15}$ alkyl benzoates, generally between about 2 to about 5%, more preferably from about 3 to about 5%.

Skin conditioners such as occlusive agents for example cyclomethicone, trimethylsiloxysilicate, glycereth-26 or polyquaternium-7 (which also functions as a film former) can be included generally in an amount of between about 1 to about 4%, more preferably between about 1 to about 3%.

Emulsifiers can be added such as cetyl alcohol, stearyl, stearic acid, glyceryl stearate, propylene glycol isostearoyl-sodium isostearoyl, a lactylate, polyoxyethylene (100) stearate.

Moisturizers such as panthenol can be included generally in amount between about 0.25 to about 1%.

Antioxidants can also be included such as tocopheryl acetate or BHT, generally in an amount between about 0.1 and about 1%, more preferably between about 0.2 and about 1%. Tocopheryl acetate if used also has anti-inflammatory properties and hence can be present for that purpose, but desirably other anti-inflammatory agents will also be present.

Humectants can also be present such as propylene glycol or glycerin generally in an amount between about 1 and about 5%, more preferably between about 3 and about 5%.

Preservatives are desirably present such as phenoxyethanol and parabens generally in an amount between about 0.5 to about 1%, more preferably between about 0.8 and about 1%.

A pH adjusting agent which will normally be a base such as triethanolamine or sodium hydroxide in an amount sufficient to provide the desired pH which will normally be between about 4 and about 5.5. This would normally be within the range of about 0.3 to about 2% depending on the acidity of the remaining ingredients.

A suitable fragrance will normally be added in an amount sufficient to give the desired pleasant aroma.

The compositions can also contain a chelating agent such as disodium EDTA or sodium citrate in an amount generally between about 0.01 and about 0.1%, more preferably about 0.05%.

The compositions can also include detackifiers such as aluminum starch octenyl succinate in an amount generally between about 1 and about 2% preferably about 1.5%.

The compositions can be in the form of a liquid with an aqueous base and a suitable organic solvent miscible with water to solubilize the lipophilic ingredients. A suitable solvent for that purpose is butylene glycol. Desirably a solubilizer such as polysorbate-20 is also included.

The compositions of the invention can also have an additional cleansing effect. Such cleansing compositions in addition to the other ingredients can include surfactants such as lauryl phosphate in an amount generally between about 2 to about 6%, more preferably between about 3 to about 5%, and a foam booster in an amount between about 2 to about 4%, more preferably between about 2.5 and about 3.5% such as cocamido propyl betaine; antibacterial agents can also be included such as triclosan in an amount generally between about 0.1 and about 0.5% preferably about 0.25%; and cleansing agents such as lauric acid and myristic acid are also desirably present generally in an amount between about 5 and about 15%, more preferably between about 8 to about 12%, most preferably between about 9 to about 10%; and The hydrolyzed soy protein of this invention produced by bacterial fermentation is supplied by Sederma under the trade mark Biodermine. It is a clear pale yellow liquid with a characteristic odor. The commercial product contains the hydrolyzed soy protein and propylene glycol.

Hydrolyzed wheat protein can be obtained from Croda as referred to above. It is a viscous amber solution with a characteristic odor. This is obtained by enzymatic hydrolysis. The product is a mixture of the hydrolyzed wheat protein in water.

The cedar wood extract and the poplar bud extract are both obtainable from Alban Muller International. The cedar wood extract is a brownish very dark greenish liquid extract from *Cedrus atlantica*. It is understood these extracts are water soluble and obtained using propylene glycol and water as the extracting solvents. It is believed that other solvents can be used to obtain extracts which will contain agents effective to control sebum in accordance with this invention.

The poplar bud extract is a brown colored liquid extracted from *populus nigra* with a balsamic odor. Again it is believed the extract so obtained uses propylene glycol and water as the extracting solvents but other extracting solvents are considered to be useful to obtain effective agents for use in this invention.

The compositions of this invention may be applied subsequent to hair removal. We believe that use of the compositions of this invention will visibly reduce ingrown hairs or bumps from shaving, waxing or use of depilatories. The compositions of this invention should not overdry the skin and should be comfortable for use in intimate areas such as the groin or underarm. They should be non-irritating, non-staining and non-greasy and preferably work to reduce ingrown hairs or bumps within a short period of time, most preferably within 24 hours of application. The compositions of this invention should act to exfoliate gently and leave skin smoother than prior to treatment. It should also reduce the appearance of redness or inflammation at the site of hair removal.

In general, the preferred ranges of concentration of the ingredients preferably utilized in the compositions and methods of this invention are as follows (all ranges are to be read as approximate):

| CTFA Name | More Preferred Range w/w | Preferred Range w/w |
| --- | --- | --- |
| Water | 70-85 | 70-85 |
| Acrylates/C10-30 alkyl Acrylate crosspolymer | 0.15-0.4 | 0.15-0.5 |
| PVM/MA Decadiene Crosspolymer | 0.5-1.3 | 0.3-1.6 |
| C12-15 Alkyl Benzoate | 2-5 | 1-5 |
| Silicones | 0.5-3 | 0.5-4 |
| Cetyl Alcohol | 0.25-2 | 0.25-3 |
| Propylene glycol | 2-5 | 1-6 |
| Salicylic acid | 0.5-2 | 0.5-2 |
| Methyl Methacrylate crosspolymer | 0.5-2 | 0.5-3 |
| Preservatives | 0.8-1 | 0.5-1 |
| Capryloylglycine/Sarcosine and cinnamon zeylanicum extract | 1-4 | 0.5-5 |
| Dipotassium glycerrhizinate | 0.1-1 | 0.05-1 |
| Panthenol | 0.2-0.5 | 0.05-1 |
| Portulaca Oleracea Extract | 0.5-1 | 0.2-3 |
| Cedarwood/hydrolyzed soy protein/hydrolyzed wheat protein | 0.5-3 | 0.1-4 |
| Alcohol | 5-10 | 3-15 |
| Tocopheryl acetate | 0.2-2 | 0.1-3 |
| pH adjustment agent | 0.1-3 | 0.1-5 |
| (−) Alpha bisabolol | 0.1-1 | 0.1-3 |
| Fragrance | 0.1-0.5 | 0.1-0.6 |
| Alcohol/witch hazel | 80-90 | 75-90 |
| Hydroxyalkylcellulose | 1-1.5 | 0.5-2 |
| Alkylene glycols | 0.5-1.5 | 0.1-3 |
| Humectant | 0.5-1 | 0.1-3 |

The following examples illustrate the methods and compositions of this invention, but do not serve to limit the scope of the invention in any way.

EXAMPLE 1

Gel compositions according to this invention were made as follows: Composition #1 was made by adding Purified Water to a mixing vessel. Acrylates C10-30 Alkyl Acrylate Crosspolymer were added to the vessel and mixed well until dispersed. Heating to about 70 to about 75° C. was started while the mixing step was carried out. At about 75 to about 80° C., PVM/MA Decadiene Crosspolymer was sprinkled into the vessel and mixed until dispersed. The vessel was then held at about 75 to about 80° C. for phasing Salicylic Acid with Propylene Glycol was pre-mixed until clear and held for addition after phasing.

An oil phase was then made in a separate vessel by adding C12-15 Alkyl Benzoate, followed by Cetyl Alcohol and heating to about 80° C. Before phasing, Cyclomethicone and Trimethylsiloxysilicate were added. In the phasing step, the water phase was transferred to a homogenizing vessel and heated. At about 70 to about 75° C., the oil phase was added to the water phase, and mixed until uniform. Half of the Sodium Hydroxide solution was added to the vessel and mixed whilst adding until a homogeneous batch was achieved. The homogenizer was turned off, the composition mixed and cooled to 55-60° C. The Salicylic acid and Propylene Glycol premix was then added and mixed until uniform. The remainder of the Sodium Hydroxide solution was added while mixing until the pH was about 4.5.

Composition #2 was made by adding Alcohol at a temperature below 40° C. with stirring. Capryloylglycine & Sarcosine & Cinnamon (*Cinnamomum Zeylanicum*) Extract was then added and the composition mixed until uniform. Portulaca extract was then added, followed by Cedarwood extract, and the composition mixed until uniform.

Composition #3 was made by further adding dipotassium glycerrhizinate to the vessel just after adding purified water. Preservatives, fragrance and tocopheryl acetate were added to Composition #1 below 40° C. Preservatives, fragrance, tocopheryl acetate and alpha bisabolol were added to Composition #2 below about 40° C. Methyl Methacrylate Crosspolymer, Phenoxyethanol and Parabens, Fragrance and Panthenol were added to Composition #3 below about 40° C. The compositions were then mixed until uniform.

Composition #4 was made in a similar manner to compositions 1-3 as a alcohol-based gel formulation and according to processes known to those of skill in the art.

Viscosity of the final compositions should be between about 5,000 and about 60,000 cps and pH measurements at 25° C. should be between about 4 and about 5.5.

Compositions 1-4 are set forth in Table IA below.

TABLE IA

| CTFA Name | #1 % w/w | #2 % w/w | #3 % w/w | #4 % w/w | Function |
|---|---|---|---|---|---|
| Water | Qs | Qs | Qs | Qs | Vehicle |
| Acrylates/C10-30 alkyl Acrylate crosspolymer | 0.30 | 0.30 | 0.30 | — | Emulsion stabilizer, Thickener |
| PVM/MA Decadiene Crosspolymer | 0.65 | 1.00 | 0.60 | — | Thickener |
| C12-15 Alkyl Benzoate | 2.50 | 2.50 | 2.50 | — | Emollient |
| Cyclomethicone & Trimethylsiloxy-silicate | 1.00 | 1.00 | 1.00 | — | Skin conditioner - occlusive |
| Cetyl Alcohol | 1.00 | 1.00 | 1.00 | — | Co-emulsifier, thickener |
| Propylene Glycol | 3.00 | 1.0 | 3.00 | 1.00 | Humectant |
| Salicylic acid | 0.50 | 0.50 | 0.50 | 2.00 | Keratolytic agent |
| Methyl Methacrylate Crosspolymer | — | — | 2.00 | — | Aesthetics control |
| Preservatives | 1.00 | 1.00 | 1.00 | — | Preservatives |
| Capryloylglycine & Sarcosine & Cinnamon (*Cinnamomum Zeylanicum*) Extract | 4.00 | 4.00 | 4.00 | 4.00 | Sebum regulator |
| Dipotassium Glycerrhizinate | — | — | 0.10 | — | Anti-inflammatory |
| Panthenol | — | — | 0.25 | — | Moisturizer |
| Portulaca Oleracea Extract | 0.50 | 0.50 | — | 0.50 | Anti-inflammatory |
| Cedarwood/HSP/HWP/Poplar Bud | 0.50 | 0.50 | — | — | Oil control/bacterial lipase inhibitor |
| Alcohol | — | 10.00 | — | 40.00 | Astringent |
| Tocopheryl Acetate | 0.25 | 0.25 | 0.25 | — | Antioxidant |
| Sodium hydroxide | 0.36 | 0.37 | 0.36 | — | Neutralizer |
| (−) Alpha Bisabolol | — | 0.20 | — | — | Anti-inflammatory |
| Fragrance | — | — | 0.08 | 0.30 | Fragrance |
| Cedarwood extract | — | — | — | 0.50 | Bacterial lipase inhibitor |
| Hamamelis Virginiana | — | — | — | 48 | Solvent |
| Hydroxyethylcellulose | — | — | — | 1.50 | Thickener |
| Butylene glycol | — | — | — | 1.00 | Solvent |
| Glcyerin | — | — | — | 1.00 | Humectant |
| Sodium citrate | — | — | — | 0.65 | Neutralizer |

EXAMPLE 2

Evaluation of Efficacy and Safety of Gel Products in the Treatment of Acne Vulgaris When Used as a Spot Treatment An evaluation of the efficacy of moisturizing gels in the treatment of acne when used as a spot treatment of compositions of this invention were tested against gels containing 10% benzoyl peroxide 2% salicylic acid.

TABLE 2

TEST GROUPS & PRODUCTS:

| Test group | Product | Active | No. of completed subjects |
|---|---|---|---|
| I | A | 10% BPO (benzoyl peroxide) | 27 |
| II | B | 2% Salicylic acid | 30 |
| III | C | Cedarwood extract + Portulaca extract + Sepicontrol A5 + Salicylic Acid | 30 |
| IV | D | Cedarwood extract + Portulaca extract + salicylic acid | 30 |
| V | E | Gel base without active ingredients | 26 |

30 females between the ages of 16 and 25, in good general health, and suffering from mild to moderate acne were selected for each of the five test groups. The number of completed subjects is stated above in Table 2. To assure uniform test parameters, all panelists were prescreened by the dermatologist at the test center.

The study incorporates a double blind, single center, parallel, randomized study design. Subjects applied the given Clean & Clear® Facial wash for two weeks prior to commencing the study, serving as a conditioning or wash out period. Test products were applied only on the acne spots twice a day (morning and evening), and recorded in a Diary Sheet, for twelve weeks. Evaluations were made during baseline and then every day for all the products for the first week and then after every two weeks up to twelve weeks of use. Dermatological assessment included global acne improvement using the global acne rating scale of 1-10 where 1=mild and 10=severe acne, and assessment for reduction in levels of oiliness and inflammation. Oiliness and inflammation were measured on a 5 point scale where 1=mild and 5=severe.

Subjects were also asked to evaluate the product after 12 weeks where they graded the product for reduction in acne, erythema, drying/peeling and oiliness also using a five point scale (1=mild, 5=severe)

The results showed that the test products as well as the controls (vehicle and benchmarks) significantly reduced the acne count only after four weeks. However, the efficacy of Composition C is faster and better (significant ~28% reduction in acne count by day 4, 40% by week 2, 56% by week 12). The benchmarks however had minimal effect on the acne count and showed significant activity only after four weeks. The Composition D only showed significant reduction in acne count (21%) by week 8 (42% reduction by week 12), 4 weeks later than 10% BPO (14% reduction by week 4, 28% reduction by week 12) and 2% salicylic acid (26% reduction by week 4, 37% reduction by week 12). Thus, the combination of Composition C unexpectedly enhanced the efficacy of the composition, particularly for an on-the-spot product. (Prior testing showed equal efficacy of Composition D with or without Sepicontrol but this could be due to full-face use; on-the-spot treatment may require a more potent combination such as Composition C).

Instrumental measurements using Sebumeter SM 810 were performed in a temperature and humidity controlled environment. The temperature was maintained by 25-28° C. and humidity within 40-60% range. These conditions were recorded during evaluation days. Subjects were instructed not to drink hot caffeinated drinks one hour before evaluation and were required to acclimatize to room conditions for at least 10 minutes prior to measurements. Sebum readings were taken by pressing the matted plastic film of the cassette with a force of 4N for 30 seconds on a designated area of the face. The skin area measured was approximately 65 $mm^2$. The cassette was then inserted into the aperture of the Sebumeter. The sebum absorbed by the film was analyzed by photometry, and the sebum reading in $\mu g/cm^2$ was then displayed and recorded. Two readings were taken on each of these test sites: left forehead, left cheek, right forehead and right cheek. Since the study was conducted during the colder months of the year, the sebum reading minimum requirement was set at 180 $\mu g/cm^2$, in order to meet the quota for the number of subjects.

Percentage sebum reduction was computed by subtracting subsequent timepoint readings from baseline reading and dividing the difference by the baseline reading. Analysis of variance was then performed on the percentage sebum reduction during weeks 3, 6, 9 and 12, with $p \leq 0.05$ used as criterion of significance.

In accordance with the results, the test products also reduced oiliness of the skin. 2% salicylic acid (Composition B) performs better in this regard (71% reduction by week 4). 10% BPO (Composition A) acts faster than Compositions C and D but is eventually matched at the end of the study (Composition A: 52% reduction, Composition C: 62%, Composition D: 45%, all by week 12). Compositions C and D, as well as the vehicle and 2% salicylic acid reduced inflammation (B: 73% reduction, C: 78%, D: 70%, E: 46%, all by week 12). Composition A, however, increased skin inflammation. Subjects who were using the product complained of severe irritation (e.g., inflammation, dryness, peeling). Three subjects from this test group were eventually dropped out from the study.

Figure 2:
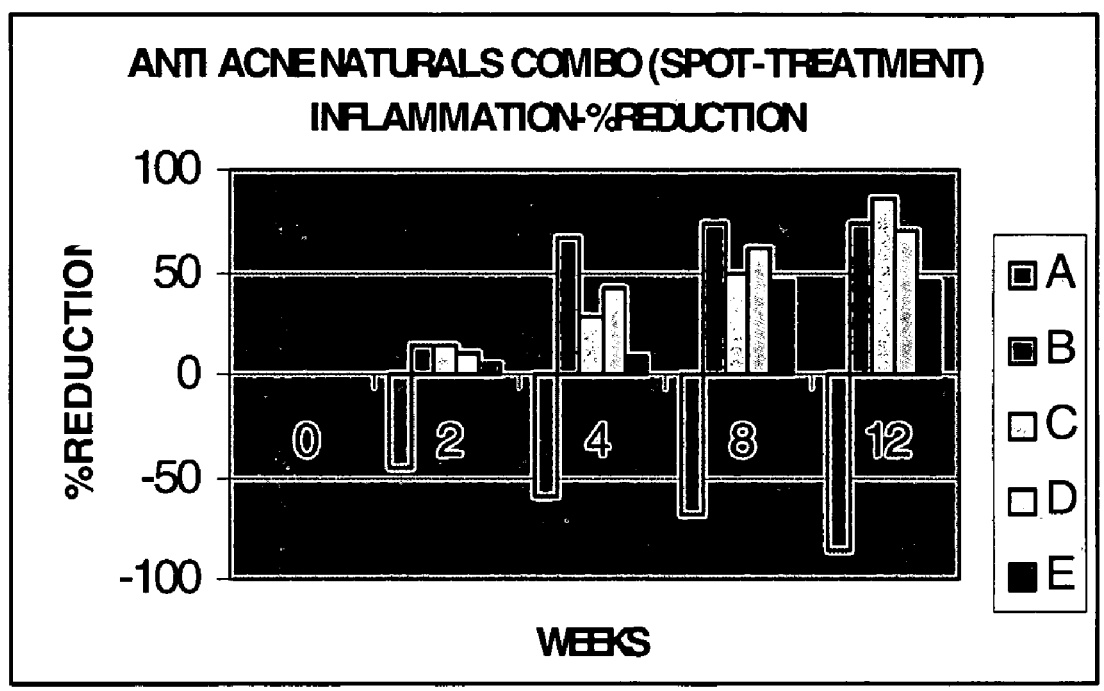
FIG. 2 is a graph illustrating the percent reduction of inflammation pursuant to testing set forth in Example 2.
Figure 3:
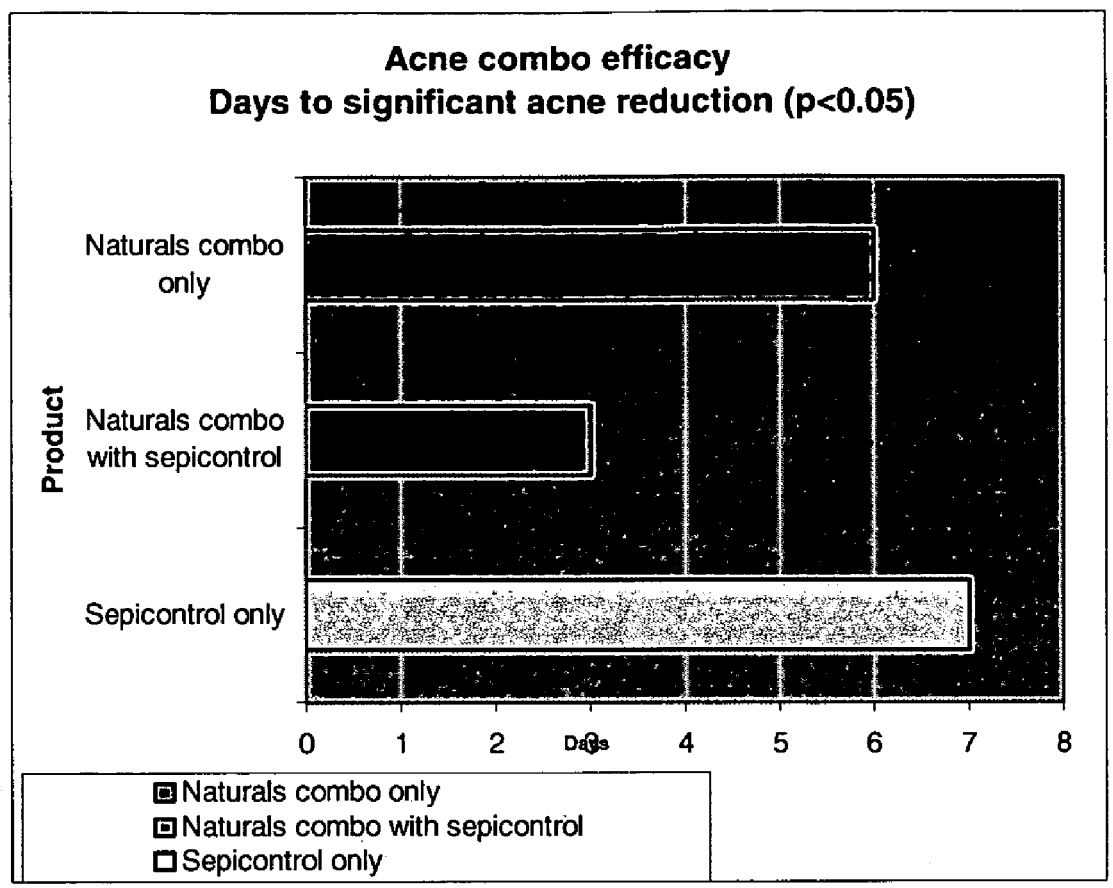
FIG. 3 is a graph illustrating the days to significant acne reduction pursuant to testing set forth in Example 3.
Figure 4:
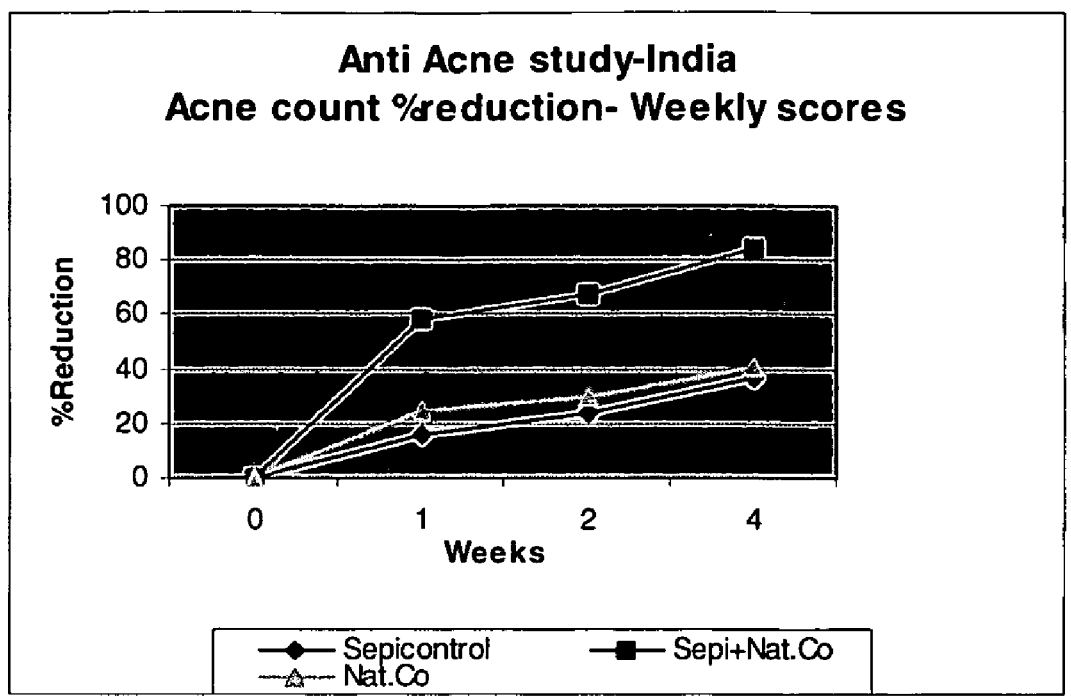
FIG. 4 is a graph illustrating the percent reduction in acne count pursuant to testing set forth in Example 3 on a weekly basis.
Figure 5:
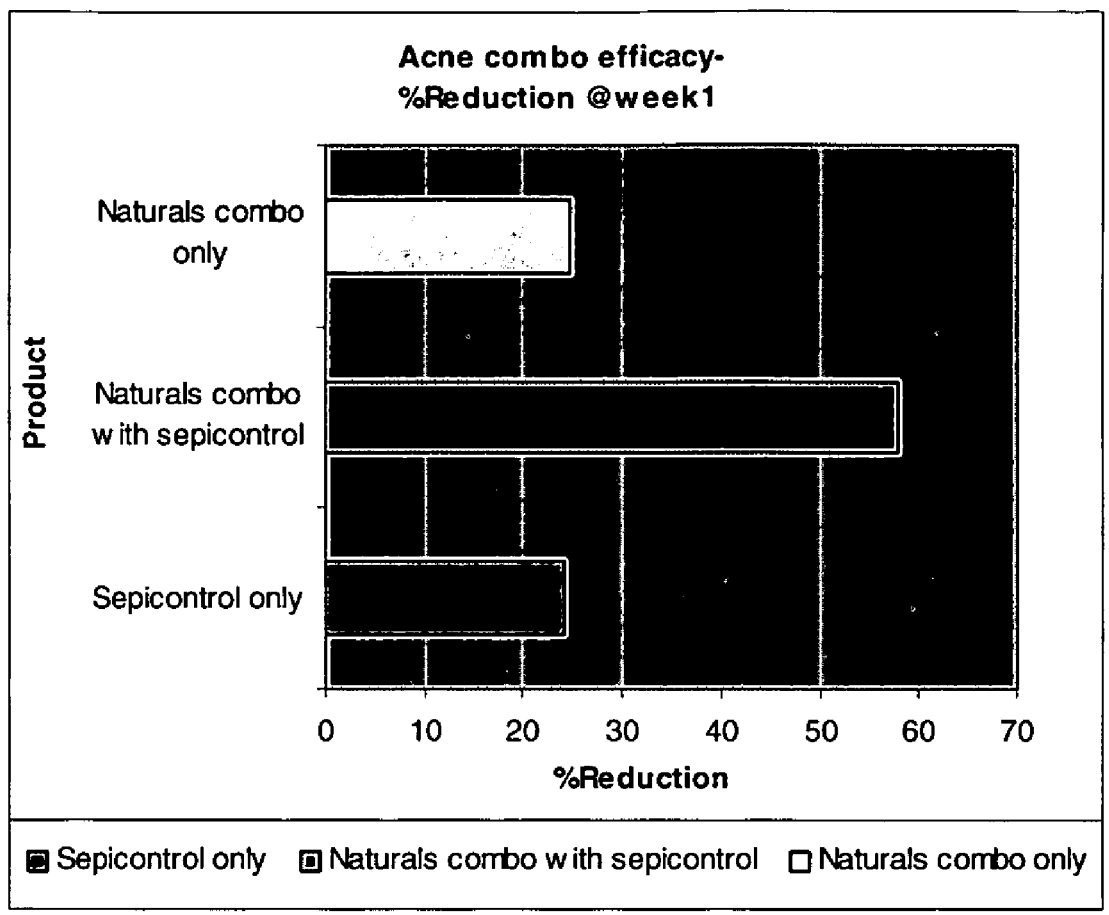
FIG. 5 is a graph illustrating the percent reduction in acne during the first week of use pursuant to testing set forth in Example 3.

Results of the test are set forth below in Tables 2A, 2B, 3 and 4 and in FIGS. 1-3.

TABLE 2A

Global Acne Assessment (Bi-weekly Scores):

| Com- position | 0 Week | 2 Weeks | | 4 Weeks | | 8 Weeks | | 12 Weeks | |
|---|---|---|---|---|---|---|---|---|---|
| | Mean | Mean | % red. | Mean | % red | Mean | % red | Mean | % red |
| A: | 4.70 | 4.39 | 6.63 | 3.90↓ | 14.06 | 3.60↓ | 19.25 | 3.26↓ | 27.87 |
| B: | 4.80 | 4.36 | 9.23 | 3.52↓ | 25.84 | 3.24↓ | 30.71 | 3.04↓ | 36.66 |
| C: | 4.46 | 2.61↓ | 40.07 | 2.26↓ | 46.08 | 2.15↓ | 48.55 | 1.88↓ | 56.11 |
| | | | abde | | abde | | ade | | ae |
| D: | 5.05 | 4.78 | 5.08 | 4.31 | 14.26 | 3.94↓ | 21.19 | 3.00↓ | 41.99 |
| E: | 4.70 | 4.55 | 2.08 | 3.90 | 19.90 | 3.60↓ | 20.16 | 3.45↓ | 22.83 |

↓ - significantly lower than baseline at 95% confidence level a, b, c, d, e - significantly better than the product code indicated at 95% confidence level

TABLE 2B

Global Acne Assessment (Daily Scores for the 1st Week):

| Composition | Day 0 Mean | Day 1 Mean | Day 2 Mean | Day 3 Mean | Day 4 Mean | Day 5 Mean | Day 6 Mean | Day 7 Mean |
|---|---|---|---|---|---|---|---|---|
| A: | 4.70 | 4.70 | 4.70 | 4.68 | 4.63 | 4.57 | 4.44 | 4.39 |
| B: 2% SAL | 4.80 | 4.80 | 4.80 | 4.75 | 4.72 | 4.62 | 4.50 | 4.36 |
| C: with Sepicontrol | 4.46 | 4.46 | 4.20 | 3.50 | 3.19↓ | 2.73↓ | 2.68↓ | 2.65↓ |
| D: without Sepicontrol | 5.05 | 5.05 | 5.00 | 4.87 | 4.75 | 4.48 | 4.27 | 3.70 |
| E: Vehicle | 4.70 | 4.70 | 4.70 | 4.70 | 4.70 | 4.70 | 4.70 | 4.70 |

↓ - significantly lower than baseline at 95% confidence level

TABLE 3

Reduction in oiliness:

| Test product | 0 W Mean | % red | 2 W Mean | % red | 4 W Mean | % red | 8 W Mean | % red | 12 W Mean | % red |
|---|---|---|---|---|---|---|---|---|---|---|
| A | 0.86 | — | 0.65 | 24.41 | 0.44 | 48.83 | 0.37 | 56.97 | 0.41↓ | 52.32 |
| B | 0.96 | — | 0.72 | 25 | 0.28↓ | 70.83 | 0.24↓ | 75 | 0.24↓ | 75 |
| C | 1.3 | — | 1.1 | 15 | 0.6 | 53.84 | 0.5↓ | 61.53 | 0.5↓ | 61.53 |
| D | 1.88 | — | 1.76 | 6.38 | 1.30↓ | 30.85 | 1.15↓ | 38.82 | 1.03↓ | 45.24 |
| E | 1.05 | — | 0.95 | 9.52 | 0.8 | 23.80 | 0.45 | 28.09 | 0.4 | 38.09 |

↓ - significantly lower than baseline at 95% confidence level

TABLE 4

Reduction in Inflammation:

| Test product | 0 W Mean | % red | 2 W Mean | % red | 4 W Mean | % red | 8 W Mean | % red | 12 W Mean | % red |
|---|---|---|---|---|---|---|---|---|---|---|
| A | 0.56 | — | 0.82 | -46.42 | 0.93 | -66 | 0.94 | -67.85 | 1.04↓ | —85..74* |
| B | 0.6 | — | 0.52 | 13.33 | 0.2 | 66.66 | 0.16 | 73.33 | 0.16 | 73.33↓ |
| C | 0.7 | — | 0.6 | 14.28 | 0.5 | 28.57 | 0.35 | 50 | 0.14 | 80.71↓ |
| D | 1.38 | — | 1.23 | 11.11 | 0.80 | 42 | 0.53 | 61.11 | 0.42 | 69.44↓ |
| E | 0.55 | — | 0.5 | 9.0 | 0.5 | 9.0 | 0.3 | 45.45 | 0.3 | 45.95↓ |

*Significant increase in inflammation

EXAMPLE 3

In this study, a comparison was made among three compositions, the first, (A) containing only Sepicontrol A5 as an active ingredient, the second, (B) containing Sepicontrol, cedarwood extract, portulaca extract and salicylic acid and the third (C) containing no Sepicontrol, but only cedarwood extract, portulaca extract and salicylic acid.

Subjects between the age of 16 to 35 years, in good general health, and suffering form mild to moderate acne were selected to participate in the study. 15 subjects were recruited per cell. There were 4 drop outs.

The study incorporates a double blind, single center, randomized, spot treatment study design. The volunteers were recruited after taking informed consent. Subjects applied the given Clean and &Clear face wash for 1 week prior to commencing the study. This was the conditioning or wash out period. Test products were applied on the acne spots only twice a day (morning and evening), and recorded in the Diary Sheet, for 4 weeks. Evaluations were made during baseline and daily for the first week (day 1,2,7). After the first week evaluation were done at the end of every week till week 4 (week 2, 3, 4).

Dermatological assessment included global acne improvement using the global acne rating scale of 1-10 where 1=mild and 10=severe acne, and assessment for reduction in levels of oiliness and inflammation. Oiliness and inflammation were measured on a 5 point scale where 1=mild and 5=severe. Subjects were also asked to evaluate the product after 4 weeks where they graded the product for reduction in acne, erythema, drying/peeling and oiliness also using a five-point scale (1=mild, 5=severe)

Results are as follows: All the test products significantly reduced the acne count at the end of 4 weeks. Composition B demonstrated significant reduction in acne count (19.35%) by Day 3 (84% reduction by week 4).

Composition A demonstrated significant efficacy (16.12% reduction) only by day 7 (37% reduction by week 4). Composition C reduced the acne count significantly (14.35%) by day 6 (42.15% reduction by week 4).

All the products were equally efficacious in reducing oiliness. Since the base was a moisturizing gel base the products did not cause excessive drying.

All the products also reduced inflammation. Composition B demonstrated better efficacy at the end of the study period, while the two other products exhibited comparable activity.

Thus, the clinical study establishes the unexpected superiority of Composition B containing a combination of natural ingredients Sepicontrol A5 in the treatment of acne vulgaris. This composition reduces the acne count significantly by day 3 as compared to day 7 by Composition A and day 6 by Composition C.

Composition B also unexpectedly offered continued improvement in the efficacy of the product. A continuous reduction in acne count was observed till the end of the study period. Composition C also demonstrated efficacy till week 4.

Composition C was marginally better than Composition A in treating acne (42% v/s 37% reduction in acne count) at the end of 4W. All the products also reduced inflammation. Composition B, however, demonstrated better efficacy at the end of the study period, while the two other products exhibited comparable activity.

As set forth below in Tables 5A, 5B,

TABLE 5A

Global Acne Assessment (First week-Daily Scores)

| Test Product | Mean Acne count | | | | | | | |
|---|---|---|---|---|---|---|---|---|
| | 0 D | 1 D | 2 D | 3 D | 4 D | 5 D | 6 D | 7 D |
| A: | 5.63 | 5.63 | 5.63 | 5.54 | 5.45 | 5.27 | 5.18 | 4.72↓ |
| B: | 4.71 | 4.71 | 4.21 | 3.78↓a | 3.50↓a | 3.14↓a | 3.07↓a | 2.07↓a |
| C: | 4.92 | 4.92 | 4.85 | 4.71 | 4.57 | 4.42 | 4.14↓ | 3.78 |

↓ - Significantly lower than baseline at 95% confidence level
a - significantly better than the product code indicated at 95% confidence level

TABLE 5B

Mean and % reduction in acne - Weekly Scores

| Test Product | Base | | 1 W | | 2 W | | 3 W | | 4 W | |
|---|---|---|---|---|---|---|---|---|---|---|
| | Mean | % red | Mean | % red | Mean | % red | Mean | % red | Mean | % red |
| A: | 5.63 | 0 | 4.27 | 16.12↓ | 4.09 | 24.19↓ | 3.54 | 37.09↓ | 3.54 | 37.09↓ |
| B: | 4.71 | 0 | 2.07 | 58.06↓a | 1.54 | 67.7↓a | 1.07 | 77.41↓a | 0.76 | 83.85↓a |
| C: | 4.92 | 0 | 3.78 | 24.47↓ | 3.5 | 30.47↓ | 3.07 | 40.73↓ | 3.00 | 42.15↓ |

↓ - significantly lower than baseline at 95% confidence level
a - significantly better than the product code indicated at 95% confidence level

TABLE 6

Percentage reduction in Inflammation - BiWeekly Scores

| Test Product | Base | | 2 W | | 4 W | |
|---|---|---|---|---|---|---|
| | Mean | % red | Mean | % red | Mean | % red |
| A: | 1.4 | 0 | 1.3 | 17.5 | 1.2 | 25↓ |
| B: | 0.8 | 0 | 0.4 | 58.38↓ | 0.2 | 64.25↓ |
| C: | 0.78 | 0. | 0.64 | 18.18 | 0.64 | 18.18↓ |

↓ - significantly lower than baseline at 95% confidence level

Figure 6:
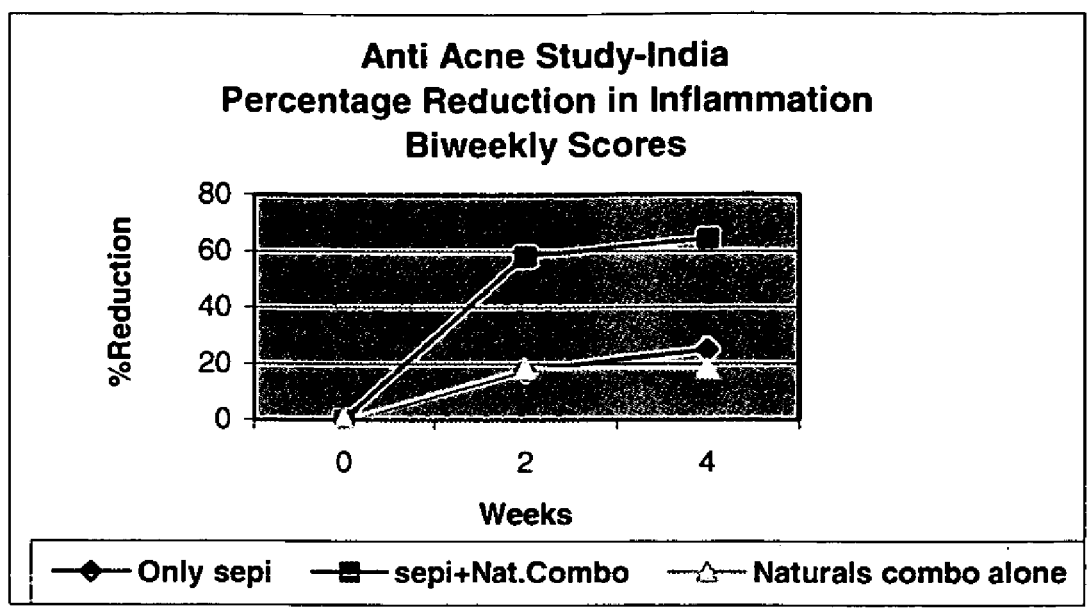
FIG. 6 is a graph illustrating the percent reduction in acne count pursuant to testing set forth in Example 3 on a biweekly basis.

The data in the above Table 6 is represented graphically in FIG. 6.

EXAMPLE 4

Compositions 5-8 below, in accordance with this invention, may be made following the procedures set forth in Example 1 having the following ingredients:

| CTFA Name | #5 w/w | #6 w/w | #7 w/w | #8 w/w | Function |
|---|---|---|---|---|---|
| Water | 60.00 | 70.10 | 70.45 | 70.45 | Vehicle |
| Acrylates/C10-30 alkyl Acrylate crosspolymers | 1.10 | 1.10 | 0.30 | 0.30 | Emulsifier |
| Xanthan gum | 0.30 | 0.30 | — | — | Thickener |
| C12-15 Alkyl benzoate | 2.50 | 2.50 | 2.50 | 2.50 | Emollient |
| Propylene glycol | — | — | — | 3.00 | Humectant |
| Silicones | 1.00 | 1.00 | 1.00 | 1.00 | Emollient |
| Cetyl alcohol | 1.50 | 1.50 | 1.00 | 1.00 | Co-emulsifier |
| Butylene glycol | 13.00 | 3.00 | | | Humectant |
| PVM/MA decadiene crosspolymer | — | — | 1.00 | 1.00 | Thickener |
| Salicylic acid | 0.50 | 0.50 | 0.50 | 0.50 | Keratolytic agent |
| Ethyl alcohol | 10.00 | 10.00 | 10.00 | 10.00 | Solubilizer |
| Glycerine | — | — | 3.00 | — | Humectant |

-continued

| CTFA Name | #5 w/w | #6 w/w | #7 w/w | #8 w/w | Function |
|---|---|---|---|---|---|
| Capryloylglycine & Sarcosine & Cinnamon (Cinnamomum Zeylanicum) Extract | 4.00 | 4.00 | 4.00 | 4.00 | Sebum regulator |
| Portulaca Oleracea | 0.50 | 0.50 | 0.50 | 0.50 | Anti-inflammatory |
| Cedarwood extract | 0.50 | 0.50 | 0.50 | 0.50 | Oil control/bacterial lipase inhibitor |

-continued

| CTFA Name | #5 w/w | #6 w/w | #7 w/w | #8 w/w | Function |
|---|---|---|---|---|---|
| Preservatives | 1.00 | 1.00 | 1.00 | 1.00 | Preservatives |
| Tocopheryl acetate | 0.25 | 0.25 | 0.25 | 0.25 | Anti-oxidant |
| Sodium hydroxide | 0.32 | 0.32 | 0.36 | 0.36 | Neutralizer |
| Alpha bisabolol | 0.25 | 0.25 | 0.20 | 0.20 | Anti-inflammatory |
| Fragrance | 0.20 | 0.20 | 0.20 | 0.20 | Fragrance |
| Disodium EDTA | 0.10 | 0.10 | — | — | Chelator |

Compositions 9-12 may also be made in accordance with the procedure set forth in Example 1, including the following ingredients:

| CTFA Name | #9 % w/w | #10 % w/w | #11 % w/w | #12 % w/w | Function |
|---|---|---|---|---|---|
| Water | Qs | Qs | Qs | Qs | Vehicle |
| Propylene Glycol | 1.00 | 1.00 | 3.00 | 1.00 | Humectant |
| Salicylic acid | 2.00 | 2.00 | 0.50 | 2.00 | Keratolytic agent |
| Capryloylglycine & Sarcosine & Cinnamon (Cinnamomum Zeylanicum) Extract | 4.00 | 4.00 | 4.00 | 4.00 | Sebum regulator |
| Portulaca Oleracea Extract | 0.50 | 0.50 | 0.50 | 0.50 | Anti-inflammatory |
| Alcohol | 30.00 | 50.00 | 40.00 | 50.00 | Astringent |
| (−) Alpha Bisabolol | 0.20 | — | 0.20 | — | Anti-inflammatory |
| Fragrance | 0.30 | — | 0.08 | 0.30 | Fragrance |
| Cedarwood extract | 0.50 | 0.50 | 0.50 | — | Bacterial lipase inhibitor |
| Hamamelis Virginiana | — | 10.00 | — | 35.00 | Solvent |
| Hydroxyethylcellulose | 1.50 | 1.50 | 1.50 | 1.50 | Thickener |
| Butylene glycol | 1.00 | 1.00 | 1.00 | 1.00 | Solvent |
| Glcyerin | 1.00 | 1.00 | 1.00 | 1.00 | Humectant |
| Sodium citrate | 0.65 | 0.65 | 0.65 | 0.65 | Neutralizer |
| Preservatives | 1.00 | — | — | — | Preservatives |

EXAMPLE 6

A double-blind, randomized study was conducted comparing the composition of Example 3B with a commercially-available acne treatment composition containing benzoyl peroxide. Sixty (60) subjects having mild to moderate acne vulgaris on the face were randomly assigned to one of two treatment groups, thirty subjects to a group. "Mild to moderate acne vulgaris was defined by 20-150 total acne lesions, of which 10-100 were non-inflammatory lesions and 10-50 were inflammatory lesions, with <1 nodule present at the baseline time. The subjects also had at least two papules or pustules on their faces in the active stage that did not yet appear to be resolving. Such papules or pustules were defined as "target lesions" for the purposes of the study.

The individuals in Group I applied the composition of Example 3B to their entire faces twice daily for a period of eight weeks. The individuals in Group II applied the benzoyl peroxide composition to their entire faces twice daily for a period of eight weeks. The individuals visited a dermatologist who performed a clinical evaluation of each test subject on days 0, 2, 4 and 7 of the study.

At the baseline visit on day 0 of the study, the dermatologist mapped the target lesions and graded each lesion according to the following scales for redness associated with the lesion, size/diameter of the lesion and swelling/height of the lesion:

| Redness Grading Scale | Size/Diameter Scale | Swelling/Height Scale |
|---|---|---|
| 0 = None | 0 = 0 mm | 0 = Completely flat |
| 1 = Slight | 1 = <2.5 mm | 1 = Slightly raised |
| 2 = Mild | 2 = 2.5-3.0 mm | 2 = Mildly raised |
| 3 = Moderate | 3 = 3.1-4.0 mm | 3 = Moderately raised |
| 4 = Severe | 4 = >4 mm | 4 = Severely raised/very swelled |

The subjects applied the designated product twice a day, in the morning and in the evening, using the following procedure: They washed their faces with PURPOSE® Gentle Cleansing Wash, rinsed thoroughly and gently patted their faces dry. They squeezed approximately ½ inch of product onto the palm of their hands and applied the product to their entire facial areas except their eye, lip and mouth areas. They allowed the product to dry for at least fifteen minutes before applying any makeup or additional facial products. They were not permitted to wash their faces for at least three hours after applying the test cream. They did not use any new facial or body products during the study. The subjects were given a diary sheet that they completed daily indicating that they performed the required product applications. They noted any unusual observations or reactions associated with the use of the products on their diary sheet.

The subjects were evaluated again on days 2, 4 and 7 of the study. The color, height and diameter of each lesion were graded and compared to earlier scores. The percent decrease in score was calculated and the results set forth in the table below, with larger decrease in scores demonstrating an improvement in the acne condition:

| | CONTROL (% improvement) | | | COMPOSITION OF INVENTION (% improvement) | | |
|---|---|---|---|---|---|---|
| Day of Study | 2 | 4 | 7 | 2 | 4 | 7 |
| Redness | 5 | 35 | 48 | 29 | 48 | 56 |
| Height | 3 | 39 | 57 | 35 | 56 | 69 |
| Diameter | 1 | 29 | 42 | 31 | 44 | 61 |

The data set forth in the table above illustrates that the compositions and methods of this invention surprisingly rapidly reduce redness associated with acne lesions, the height of such lesions and the diameter of such lesions compared with a commercially available acne treatment. Unexpectedly, the compositions and methods of this invention resulted in a significant reduction of each characteristic even at the Day 2 follow visit, while the commercially-available product did not evidence such an improvement until the Day 4 follow up visit.

EXAMPLE 7

Mitigation of Ingrown Hairs and Razor Bumps

A small scale home use test is performed to determine if consumers perceive a benefit to using the compositions of this invention. The study design is a two-cell monadic study. Two compositions of this invention are utilized in a blinded study. The first composition to be used is Clean & Clear® Advantage Daily Acne Clearing Lotion; the second composition to be used is Clean & Clear® Advantage Daily Acne Spot Treatment. Both compositions are commercially available from Johnson & Johnson Consumer Products Company (Skillman, N.J.). About 100 women between the ages of 18 and 40 are sought for participation in the study. Each cell will have 50 women.

The women should shave or groom the bikini area (i.e., the area of pubic hair on or adjacent to the perineum) on a regular basis at least once per week throughout the year. They should experience ingrown hair or red bumps related to shaving the bikini area.

Those individuals who are participating in the cell utilizing the Clean & Clear® Advantage Daily Acne Spot Treatment should make sure the skin to be treated is clean and dry, first testing a small area of the skin for sensitivity. The Clean & Clear® Advantage Daily Acne Spot Treatment should be applied to the affected skin in the bikini area one to two times daily.

Those individuals who are participating in the cell utilizing the Clean & Clear® Advantage Daily Acne Clearing Lotion should make sure the skin to be treated is clean and dry, first testing a small area of the skin for sensitivity. The Clean & Clear® Advantage Daily Acne Clearing Lotion should be gently massaged over the skin in the bikini area after hair removal one to two times daily. The Clean & Clear® Advantage Daily Acne Clearing Lotion should be used as a regular part of the hair removal routine, whether the hair is removed by razor, wax or depilatory.

We believe that the use of the Clean & Clear® Advantage Daily Acne Clearing Lotion and Clean & Clear® Advantage Daily Acne Spot Treatment will visibly reduce ingrown hairs and bumps that occur due to shaving, waxing or use of depilatories. We believe that the skin will evidence visible improvement within 24 hours of first use and that the products will be safe for use in the bikini area without overdrying or creating a stinging sensation on the skin. The compositions of this invention should be non-irritating, non-staining, non-greasy and fast acting. They should gently exfoliate the skin, leaving it smoother than before use and should reduce the appearance of redness on the skin. The Clean & Clear® Advantage Daily Acne Clearing Lotion should be fast-absorbing and lightweight. It should, with regular use, help prevent ingrown hairs and bumps from developing.

What is claimed is:

1. A method of treating the development of ingrown hairs or razor bumps due to hair removal, in patients in need thereof, comprising the topical application of a composition to a skin area that has been subjected to hair removal techniques, said composition comprising cedarwood extract, salicylic acid and portulaca extract.

2. A method according to claim 1 wherein said composition further comprises caprylol glycine, sarcosine, cinnamon extract, and a mixture thereof.

3. A method of treating the development of ingrown hairs and razor bumps due to hair removal, in patients in need thereof, comprising the topical application of a composition to a skin area that has been subjected to hair removal techniques comprising (i) caprylol glycine, sarcosine, cinnamon extract, and a mixture thereof, (ii) portulaca extract, and (iii) salicylic acid.

4. A method according to claim 3 wherein said composition further comprises a bacterial lipase inhibitor selected from the group consisting of: hydrolyzed wheat protein, hydrolyzed soy protein, cedarwood extract and combinations thereof.

5. A method according to claim 3 wherein said composition further comprises a bacterial proliferation inhibitor selected from the group consisting of: tea tree oil, erythromycin, clindamycin, and combinations thereof.

* * * * *